(12) United States Patent
Collaert et al.

(10) Patent No.: US 10,309,925 B2
(45) Date of Patent: Jun. 4, 2019

(54) FET BIOSENSOR

(71) Applicant: IMEC VZW, Leuven (BE)

(72) Inventors: Nadine Collaert, Blanden (BE); Voon Yew Thean, Tervuren (BE)

(73) Assignee: IMEC vzw, Leuven (BE)

( * ) Notice: Subject to any disclaimer, the term of this patent is extended or adjusted under 35 U.S.C. 154(b) by 384 days.

(21) Appl. No.: 15/143,262

(22) Filed: Apr. 29, 2016

(65) Prior Publication Data

US 2016/0320336 A1 Nov. 3, 2016

(30) Foreign Application Priority Data

Apr. 30, 2015 (EP) .................................... 15166077

(51) Int. Cl.

| G01N 27/414 | (2006.01) |
|---|---|
| H01L 21/265 | (2006.01) |
| H01L 29/423 | (2006.01) |
| H01L 29/66 | (2006.01) |

(52) U.S. Cl.
CPC ....... G01N 27/4145 (2013.01); G01N 27/414 (2013.01); H01L 21/26586 (2013.01); H01L 29/42356 (2013.01); H01L 29/6653 (2013.01)

(58) Field of Classification Search
CPC . G01N 27/41–27/4148; H01L 29/6653; H01L 29/42356; H01L 21/26586
See application file for complete search history.

(56) References Cited

U.S. PATENT DOCUMENTS

| 8,513,102 B2 | 8/2013 | Forbes et al. |
| 2010/0055699 A1 | 3/2010 | Kahya |
| 2012/0282596 A1 | 11/2012 | Khater et al. |
| 2013/0214332 A1 | 8/2013 | Wu |
| 2013/0291627 A1 | 11/2013 | Hu et al. |
| 2014/0061728 A1 | 3/2014 | Trivedi |

OTHER PUBLICATIONS

Buitrago et al. "Electrical characterization of high performance, liquid gated verticallystacked SiNW-based 3D FET biosensors", Sensors and Actuators B 199 (2014): 291-300, Apr. 3, 2014.
Buitrago et al. "Junctionless silicon nanowire transistors for the tunable operation of a highly sensitive, low power sensor", Sensors and Actuators B 183 (2013): 1-10, Apr. 5, 2013.
Buitrago et al. "The top-down fabrication of a 3D-integrated, fully CMOS-compatible FET biosensor based on vertically stacked SiNWs and FinFETs", Sensors and Actuators B 193 (2014): 400-412, Dec. 11, 2013.
Rigante et al. "FinFET for high sensitivity ion and biological sensing applications", Microelectronic Engineering 88 (2011): 1864-1866, Dec. 25, 2010.

*Primary Examiner* — J. Christopher Ball
(74) *Attorney, Agent, or Firm* — Knobbe, Martens, Olson & Bear LLP

(57) ABSTRACT

The disclosed technology relates generally to semiconductor devices, and more particularly to semiconductor devices such as field-effect transistor devices configured for biomolecule sensing. In one aspect, a semiconductor chip comprises at least one field-effect transistor device which comprises a source, a drain, a gate stack and a channel region formed between the source and the drain. The gate stack only partially overlaps the channel region at the source side and/or at the drain side, such that a non-overlapped channel region at the source side and/or at the drain side is formed, where the non-overlapped channel region is configured for sensing biomolecules.

18 Claims, 10 Drawing Sheets

FET BIOSENSOR

CROSS-REFERENCE TO RELATED APPLICATIONS

This application claims foreign priority to European Patent Application EP 15166077.6, filed Apr. 30, 2015, the content of which is incorporated by reference herein in its entirety.

BACKGROUND

Field

The disclosed technology relates generally to semiconductor devices, and more particularly to semiconductor devices such as field-effect transistor devices configured for biomolecule sensing. The disclosed technology also relates to methods of fabricating and using the same.

Description of the Related Technology

Prior art nanowires and FinFET-based multigate devices are interesting device architectures for biosensing applications. Such devices show a high sensitivity, since the binding of biological molecules at the surface thereof can significantly affect the conduction path in these devices, does influencing measurement results. They sense biomolecules at a surface (captured from a solution) by exposing the gate of the device to a solution comprising the charged biomolecules.

A FinFET device acts as a transducer, translating and amplifying the difference in charge to a difference in conductance. The gate often comprises antibodies which are able to bind with particular biomolecules. In order to increase the sensitivity, these devices are often operated in the sub-threshold regime by applying a voltage on a back gate. In the sub-threshold regime the current through the drain is exponentially dependent on the voltage of the gate and therefore in this region the sensitivity is increased.

So far, the use of nanowires, both silicon and non-silicon based, has been limited to label-free sensing of biomolecules. Nowadays, there is also an increasing need for techniques that can sequence DNA in a very quick and cheap way. Sequencing involves determining the order of the bases Adenine, Cytosine, Guanine and Thymine in a gene or on a chromosome. Typically optics-based sequencing methods are used. These methods, although considered to have a very high accuracy, are very expensive, and hence are to be avoided if possible. Single-molecule sequencing technologies, such as nano-pores, can potentially be used to sequence long strands of DNA without labels or amplification. The main challenge is to distinguish the different nucleobases, as typically the difference is very small and for that purpose the controllability and reproducibility of nanopores is key.

In view of these applications (DNA and protein sequencing and in general biomolecule sensing) there is a need for good biosensing devices, i.e. biosensing devices with good sensitivity, which are preferably inexpensive.

SUMMARY OF CERTAIN INVENTIVE ASPECTS

It is an object of embodiments of the present disclosed technology to provide sensitive chips for biosensing.

The above objective is accomplished by a method and device according to the present disclosure.

In a first aspect, the present disclosure provides a method for producing a semiconductor chip configured for biosensing. The method comprises: obtaining a substrate comprising at least one semiconductor layer, providing a gate stack, including gate dielectric and gate electrode material, on the substrate, providing a doped drain region in and/or on the substrate, and providing a doped source region in and/or on the substrate, such that there is an underlap region between the gate stack and the source region and/or between the gate stack and the drain region, such that the underlap region is suitable for sensing biomolecules.

It is an advantage of embodiments of the present disclosure that sensitive chips for bio-sensing can be produced. The biosensing chips are highly sensitive, and allow to sense the presence of a small amount of biomolecules, which may be present only very locally. It is an advantage of embodiments of the present disclosure that a direct contact between the biomolecules and the underlap region is possible. It is thus an advantage of embodiments of the present disclosure that the underlap region is capable of sensing biomolecules. The presence of biomolecules changes the gate—source or gate—drain underlap, and therefore changes the drain current. Changing the gate—source or gate—drain underlap changes the external resistance in the source and/or drain by whether or not having an overlap between gate and source and/or gate and drain. It is an advantage of embodiments of the present disclosure that large scale manufacturing of semiconductor chips according to embodiments of the present disclosure is possible. It is an advantage of embodiments of the present disclosure that these devices can be integrated with CMOS read-out circuits.

In a method according to embodiments of the present disclosure, providing a doped source region and/or providing a doped drain region in or on the substrate, such that there is an underlap region between the gate stack and the source region or such that there is an underlap region between the gate stack and the drain region may include performing a tilted implantation.

It is an advantage of embodiments of the present disclosure that no deposition of further materials is required. The height of the gate stack and the tilt of the implant define the dimensions of the underlap region. By applying the doping in a tilted way, the drain region can be made overlapping with the gate stack.

In a method according to embodiments of the present disclosure, providing a doped source region and providing a doped drain region in or on the substrate such that there is an underlap region between the gate stack and the source region and/or such that there is an underlap region between the gate stack and the drain region includes, may comprise, before actually providing the doped source region, providing a spacer next to the gate stack at the side oriented towards the source region and/or a spacer next to the gate stack at the side oriented towards the drain region.

It is an advantage of embodiments of the present disclosure that a spacer can be used to block doping material from entering the semiconductor layer. Afterwards the spacer material can be removed such that the bio-molecules have direct access to the undoped channel. The spacer width defines the dimensions of the underlap region.

Providing a doped source region and/or providing a doped drain region in or on the substrate may comprise growing an in-situ doped semiconductor layer. By growing an in-situ doped semiconductor layer, defects may be minimized.

Alternatively, providing a doped source region and/or providing a doped drain region in or on the substrate may comprise depositing doped spin on glass, and outdiffusing the dopants into the source and/or drain region. This way, the number of defects in the source and drain areas can be limited or reduced.

A method according to embodiments of the present disclosure may furthermore comprise, after provision of the doped source region and of the doped drain region, removing the spacer at the side of the gate stack oriented towards the source region and/or removing the spacer at the side of the gate stack oriented towards the drain region.

A method according to embodiments of the present disclosure may further comprise BEOL processing of the semiconductor chip.

In a method according to embodiments of the present disclosure, providing a doped drain region may include covering the source side such that the source side of the substrate is not doped. It is an advantage of embodiments of the present disclosure that only the drain side of the substrate may be doped, such that an undoped part is obtained in the source to modulate the resistance there.

In a second aspect, the present disclosure provides a semiconductor chip configured for bio-sensing. The semiconductor chip comprises: at least one FET device comprising a source, a drain, a gate stack, and a channel region between the source and the drain, such that the gate stack is only partially overlapping the channel region at the source side and/or at the drain side and the non-overlapped channel region at the source side and/or at the drain side is suitable for sensing biomolecules. It is an advantage of embodiments of the present disclosure that the presence of biomolecules at the open side of the channel changes the effective overlapping between the gate stack and the channel. The proximity between the sensor and the biomolecule is advantageous in view of the sensitivity of the semiconductor.

In a semiconductor chip according to embodiments of the present disclosure, a spacer may be present between the gate stack and the drain on the substrate.

In a semiconductor chip according to embodiments of the present disclosure, the gate stack may be overlapping the drain.

A semiconductor chip according to embodiments of the present disclosure may moreover comprise a reference FET for which the gate stack is completely overlapping the channel. The reference FET can be used to compensate for drift occurring in both the reference FET and the FET with partially covered channel.

In a semiconductor chip according to embodiments of the present disclosure, the FET may comprise a backgate. It is an advantage of embodiments of the present disclosure that the sub-threshold sweep can be modified by adjusting the backgate voltage of the FET.

In a semiconductor chip according to embodiments of the present disclosure, the channel region may have an increased body factor. It is an advantage of embodiments of the present disclosure that the sub-threshold swing can be lowered by using the parasitic bipolar transistor of the FET. For that purpose the body factor of the channel region is increased. The steepness of the sub-threshold slope can be increased by using the parasitic bipolar transistor in the FET device.

In a further aspect, the present disclosure provides the use of a semiconductor chip according to any of the embodiments of the second aspect of the present disclosure, for biomolecule sensing. It is an advantage of embodiments of the present disclosure that sensitive measurements of biomolecules can be done. The semiconductor chip may comprise a backgate and the sub-threshold sweep may be adjusted by adjusting the voltage of the backgate. It is an advantage of embodiments of the present disclosure that the semiconductor chip can be biased in the sub-threshold regime, which increases the sensitivity of the semiconductor chip for sensing the presence of bio-molecules. It is an advantage of embodiments of the present disclosure that the voltage range and sub-threshold slope can be changed by the back bias voltage. It is an advantage of embodiments of the present disclosure that the biasing scheme can be adjusted to the kind of sensing needed: for example label-free sensing of biomolecules but also possibly DNA sequencing where small differences in the order of $\mu V$ and mV need to be sensed.

Particular and preferred aspects of the disclosure are set out in the accompanying independent and dependent claims. Features from the dependent claims may be combined with features of the independent claims and with features of other dependent claims as appropriate and not merely as explicitly set out in the claims.

These and other aspects of the disclosure will be apparent from and elucidated with reference to the embodiment(s) described hereinafter.

Figure 1:
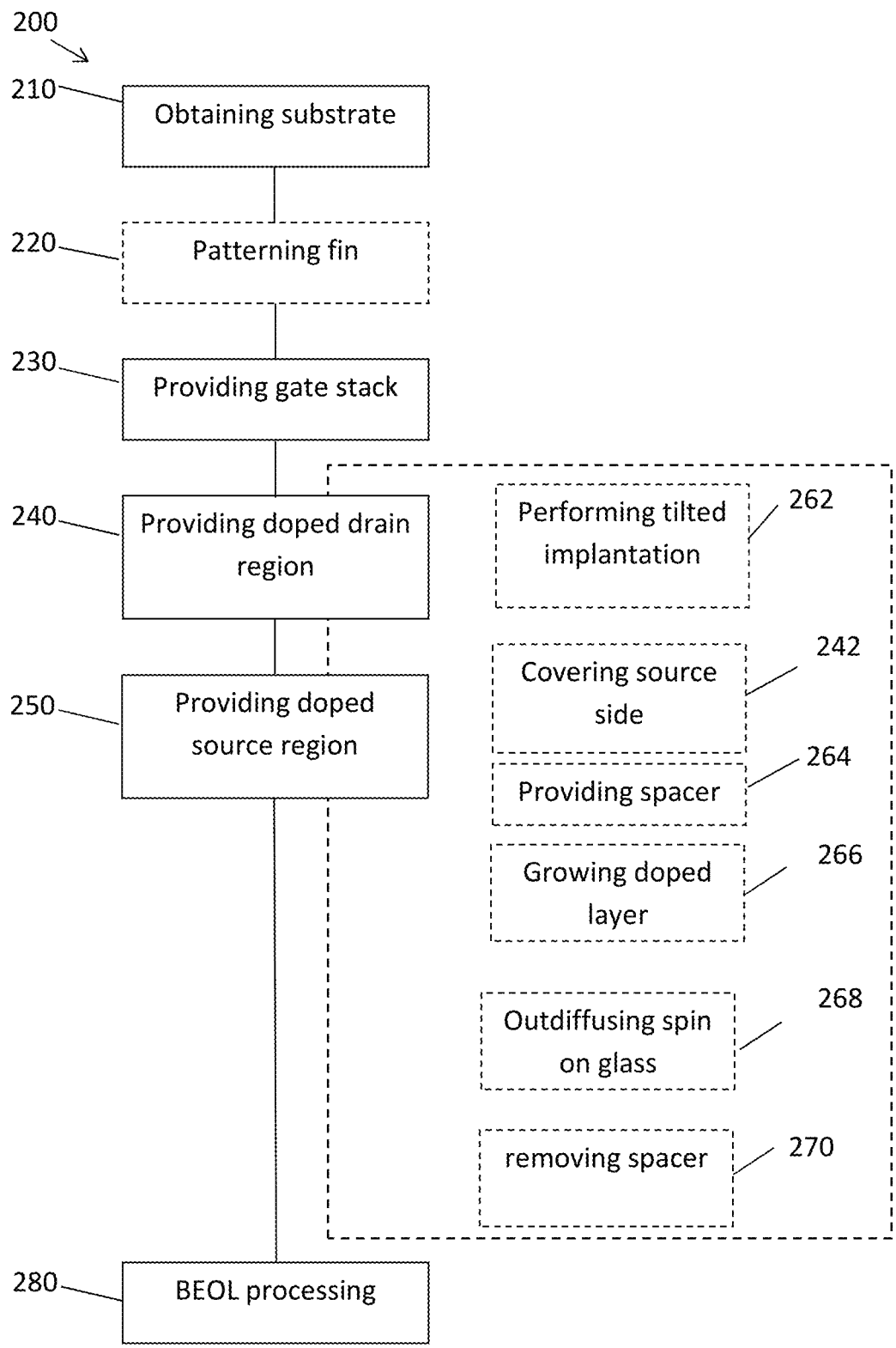
FIG. 1 is a flow chart illustrating a method of fabricating a semiconductor chip configured for bio-sensing, in accordance with embodiments of the present disclosure.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF CERTAIN ILLUSTRATIVE EMBODIMENTS

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the disclosure.

Moreover, the terms top, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed disclosure requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

In a first aspect, the present disclosure relates to a method 200 for producing a semiconductor chip 100, according to embodiments. The chip 100, as for instance illustrated in top view in FIG. 2 and in cross-sectional view in FIG. 3, can be used for bio-sensing applications. The method 200 according to embodiments of the present disclosure can be used to fabricate field-effect transistor (FET) devices, e.g., FinFET devices. The FET devices can be, e.g., bulk FinFET devices, silicon on insulator (SOI) FinFET devices, or tunnel FET (TFET) devices. The different processes in accordance with embodiments of the present disclosure are illustrated in FIG. 1.

The method 200 comprises a process 210 wherein a substrate comprising at least one semiconductor layer is obtained. In embodiments of the present disclosure, the term "substrate" may include any underlying material or materials (underlying substrate) that may be used, or upon which at least one semiconductor layer may be provided. In particular embodiments, this "substrate" may include a semiconductor substrate such as e.g. a doped or undoped silicon, a gallium arsenide (GaAs), a gallium arsenide phosphide (GaAsP), an indium phosphide (InP), a germanium (Ge), or a silicon germanium (SiGe) substrate. The "substrate" may include, for example, an insulating layer such as a $SiO_2$ or a $Si_3N_4$ layer in addition to a semiconductor substrate portion. Thus, the term substrate can also include semiconductor-on-glass (e.g. silicon-on-glass) substrates or semiconductor-on-sapphire (e.g. silicon-on sapphire) substrates. The term "substrate" is thus used to define generally the elements for layers that underlie a layer or portions of interest. Also, the "substrate" may be any other base on which a semiconductor layer is formed, for example a glass or metal layer.

In the following, aspects of the present disclosure will be explained referring to the manufacturing of a FinFET device; the present disclosure, however, not being limited thereto. In alternative embodiments of the present disclosure, other types of FET devices may be manufactured as biosensing devices, for instance TFET devices.

Figure 2:
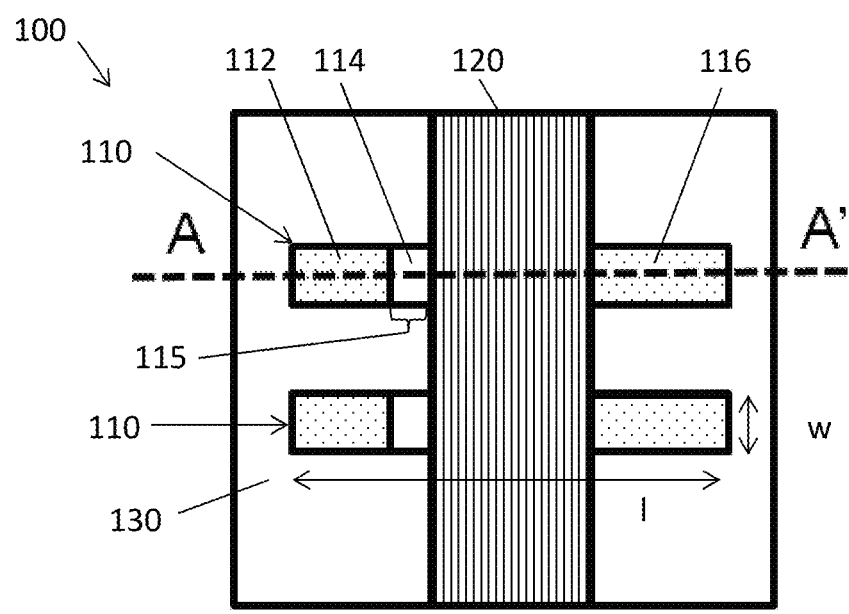
FIG. 2 is a schematic drawing of a top view of a semiconductor chip configured for biosensing, according to an exemplary embodiment of the present disclosure.
Figure 4:
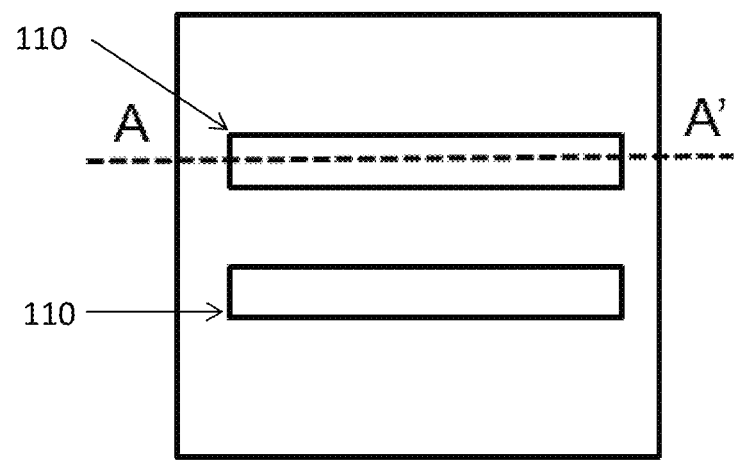
FIG. 4 is a schematic drawing of a semiconductor chip after patterning two fins in the semiconductor layer in accordance with embodiments of the present disclosure.
Figure 5:
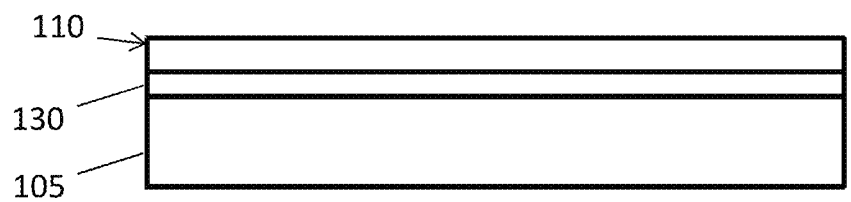
FIG. 5 shows the cross-section AA' of the exemplary embodiment of FIG. 4.

After obtaining 210 the substrate with the semiconductor layer, in some embodiments, optionally, e.g., in the particular case of manufacturing a FinFET, the present disclosure not being limited thereto, at least one fin 110 may be patterned 220 in the semiconductor layer. The at least one fin has a length dimension 1 and a width dimension w in the plane of the semiconductor layer, as illustrated in FIG. 2. FIG. 4 shows a schematic drawing of a (part of a) semiconductor chip after patterning 220 two fins 110 in the semiconductor layer. FIG. 5 shows a vertical cross-section of the same semiconductor chip along the AA' section shown in FIG. 4. It shows the semiconductor fins 110, e.g. silicon fins, on top of a dielectric layer 130, e.g. an oxide layer, on top of an underlying substrate 105, for instance a further silicon layer. In an exemplary embodiment, the substrate, comprising the underlying substrate 105, the dielectric layer 130 and the semiconductor layer of which the fins 110 are manufactured, may be of the silicon-on-insulator (SOI) type, more specifically of the ultra-thin buried oxide (UTBOX) SOI type.

Figure 6:
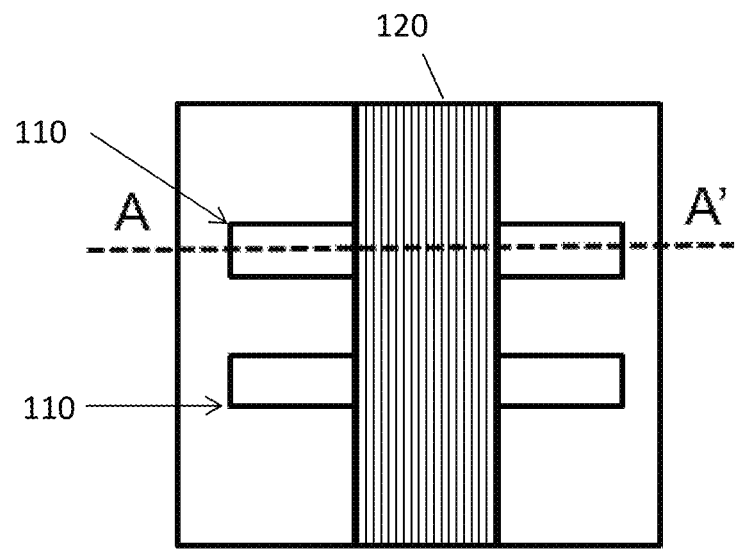
FIG. 6 shows a schematic drawing of a semiconductor chip after providing a gate stack over the two fins in accordance with embodiments of the present disclosure.
Figure 7:
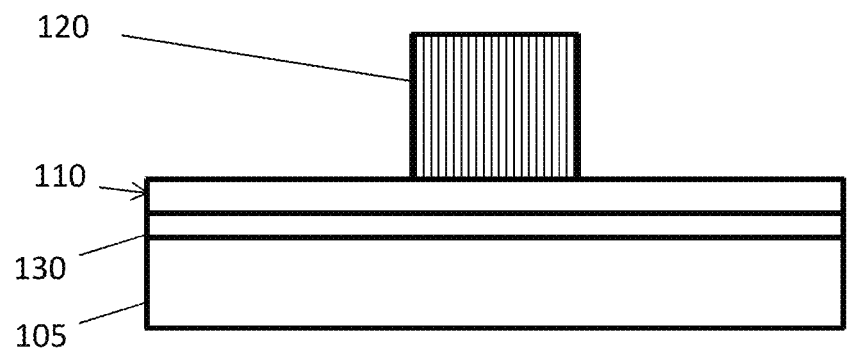
FIG. 7 shows the cross-section AA' of the exemplary embodiment of FIG. 6.

The method 200 comprises a next process 230 wherein a gate stack 120, comprising gate dielectric and a gate electrode, is provided on the substrate. In case at least one fin 110 was patterned during the optional previous method process 220, the gate stack 120 is provided over the at least one fin 110, such that the gate stack 120 partially covers the fin 110 in its length dimension 1. Providing a gate stack 120 on the substrate may include depositing a layer of gate dielectric material and a layer of gate electrode material over the complete substrate, and patterning the gate stack such that gate (dielectric and electrode) material is removed from places where it should not be present. FIG. 6 shows a schematic top view of a semiconductor chip after providing 230 a gate stack 120 over the two fins 110. FIG. 7 shows a cross-section of the same semiconductor chip as in FIG. 6 along the AA' line shown in FIG. 6. The gate stack 120 partially covers the fin 110 in its length dimension 1, and where present, completely covers the fin 110 in its width direction w. In fact, the gate stack 120 is provided such that it covers three sides of the fin 110. In the embodiment of the present disclosure illustrated in the drawings, the gate stack 120 is crossing the fins 110 orthogonally.

In alternative embodiments, not illustrated in the drawings, where rather than FinFET devices, other types of FET devices, such as TFET devices, are manufactured, the substrate may comprise a semiconductor layer with a dielectric layer on top, and the gate electrode may be provided on top of the dielectric layer, which forms the gate dielectric. The gate electrode and the gate dielectric together form the gate stack.

Figure 8:
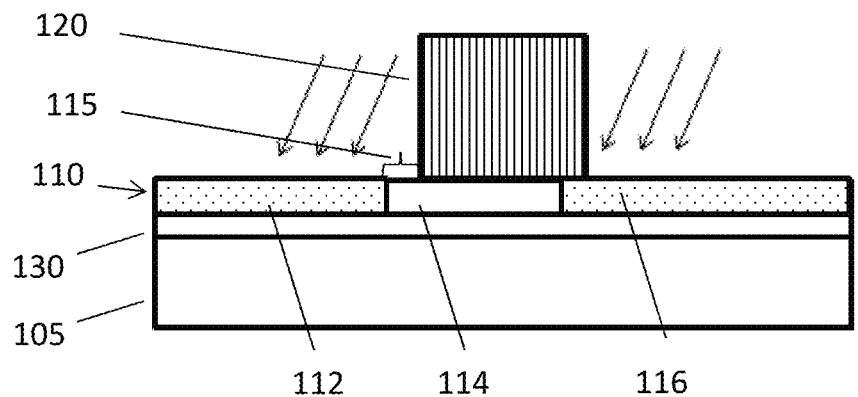
FIG. 8 illustrates tilted implantation for providing the doped source region and for providing the doped drain region in accordance with embodiments of the present disclosure.

After providing 230 the gate stack 120, doped regions are provided. A doped drain region 116 is provided 240 in and/or on the substrate and a doped source region 112 is provided 250 in and/or on the substrate. Both are provided such that an underlap region 115 is present between the gate stack 120 and the source region 112 and/or between the gate stack 120 and the drain region 116. In FIG. 8, for illustrative purposes only, the underlap region 115 is illustrated to be present at the side of the source region 112. However, the underlap region can be present at the side of the drain region 116, or at the sides of the source region 112 and the drain region 116. The underlap region 115 is provided such that it is suitable for sensing biomolecules. This includes that the underlap region 115 has dimensions suitable for sensing biomolecules.

Providing the doped regions 112, 116 may comprise different substeps. The doped drain region 116, 1216 may be provided in and/or on the substrate, for instance in and/or on the fin 110. In the embodiment illustrated in FIG. 8, the doped drain region 116 is provided in the fin 110. In an alternative embodiment as for example illustrated in FIG. 13, the drain region 116, 1216 is provided partly in the fin 116 (part 116 of the drain region), and partly on top thereof (part 1216 of the drain region), as will be explained below in more detail. In yet alternative embodiments, the drain region may formed on top of the fin. In still alternative embodiments, no fin may be present, and the drain region may be formed in, on, or partly in and partly on the substrate.

Similarly, the doped source region 112, 1212 may be provided in and/or on substrate, for instance in and/or on the fin 110. In the embodiment illustrated in FIG. 8, the doped source region 112 is provided in the fin 110. In an alternative embodiment as for example illustrated in FIG. 13, the source region 1212 is provided on top of the fin 110, as will be explained below in more detail. In yet alternative embodiments, the source region may be a combination of a part formed in the fin, and a part formed on top of the fin. In still alternative embodiments, no fin may be present, and the source region may be formed in, on, or partly in and partly on the substrate.

In various embodiments of the present disclosure, the doped source region and/or the doped drain region may be provided 240, 250 using tilted implantation 262. FIG. 8 illustrates tilted implantation 262 for providing 250 the doped source region and for providing 240 the doped drain region. During the tilted implantation 262, the gate stack 120 blocks a part of the underlying substrate, for instance the fin 110, from being directly exposed to the implantation elements. This way, the doped region formed by the implantation elements, e.g., the doped source region 112 in the embodiment illustrated in FIG. 8, is laterally separated from, or not contiguous with, the gate stack 120, due to the presence of an underlap region 115 therebetween. The angle of the tilted implantation and the height of the gate stack 120 define the underlap region 115 between the gate stack 120 and the source region 112.

Figure 9:
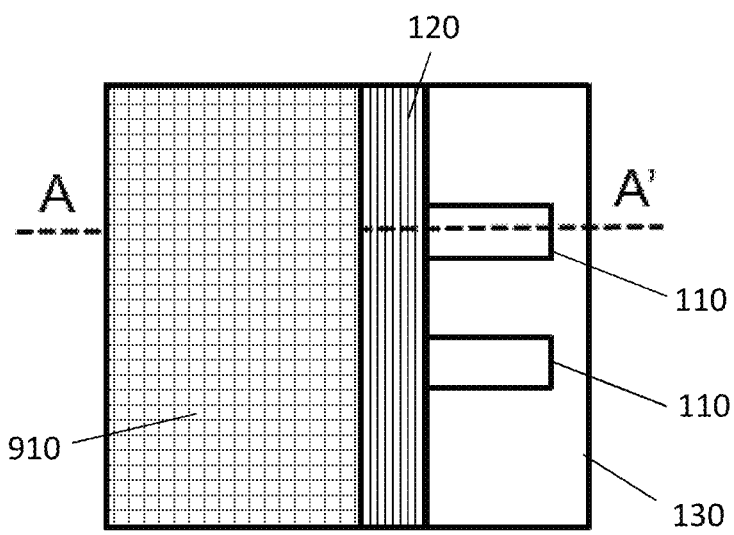
FIG. 9 shows an intermediate semiconductor chip in accordance with embodiments of the present disclosure during a process whereby the source side is covered before providing a doped drain region.
Figure 10:
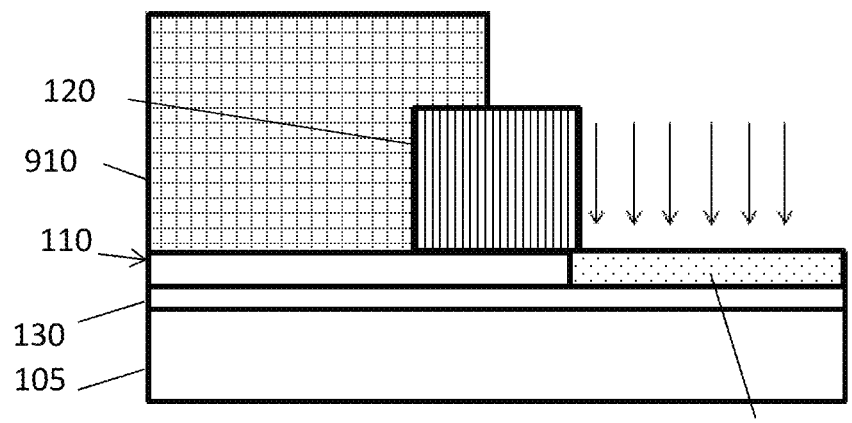
FIG. 10 shows the cross-section AA' of the exemplary embodiment of FIG. 9.

In alternative embodiments of the present disclosure, as illustrated in FIG. 9 and FIG. 10, providing a doped drain region 116 includes covering 242 the source side such that the source side in the substrate/fin is not doped with the drain region 116. FIG. 9 and FIG. 10 show a method process 242 whereby the source side is covered before providing 240 a doped drain region 116 in the fin 110. This prevents doping the source side 112 in the fin 110 when providing a doped drain region 116. The cover 910 is shown in FIG. 9 and in FIG. 10. The cover can be made of any suitable material which prevents dopant elements to travel there through and into a layer underneath, such as for instance amorphous carbon, nitride, oxide or a combination of nitride and oxide. The cover material can be selectively deposited onto the regions to be protected from dopants, or can be deposited as a blanket layer over substantially the whole substrate, and can be selectively removed thereafter, so as to only remain on one or more areas to be protected from dopant implantations. After the dopant implantation in the drain region 116, the cover 910 may be completely removed again.

Figure 11:
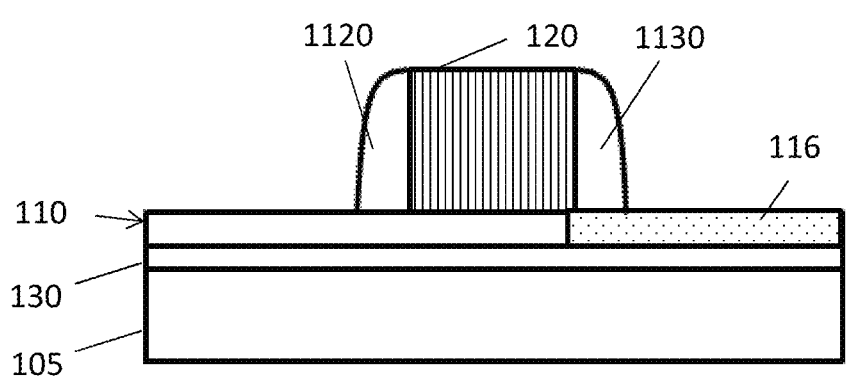
FIG. 11 illustrates an intermediate semiconductor chip, in accordance with embodiments of the present disclosure, after providing spacers next to the gate stack.

Referring to FIG. 11, in some embodiments of the present disclosure where an underlap 115 is be provided between source region 112 and gate stack 120, at least a spacer 1120, which can be a sacrificial spacer 1120, is provided 264 next to the gate stack 120 at the side oriented towards the source region 112. Furthermore, a further spacer 1130 may be provided 264, but does not need to be provided, next to the gate stack oriented towards the drain region 116. The spacers 1120, if present, are provided before actually providing 250 the doped source region, e.g. before the actual implantation process. FIG. 11 illustrates an intermediate semiconductor chip after providing 264 the spacers 1120, 1130 next to the gate stack 120. In this example the spacers are provided after having provided 240 the doped drain region 116. When actually providing the doped source region, for instance by dopant implantation, the spacer 1120 located at the side where the source region 112 has to come, protects the underlying substrate, e.g. fin 110, from source dopants. When thereafter removing the spacer 1120, a gap is left between the gate stack 120 and the source region. 112, resulting in an underlap region 115, similar to the intermediate semiconductor chip 100 illustrated in FIG. 3. The width of the underlap region 115 is about equal to the width of the spacer 1120 which has been removed from next to the gate stack at the side oriented towards the source 112.

Figure 19:
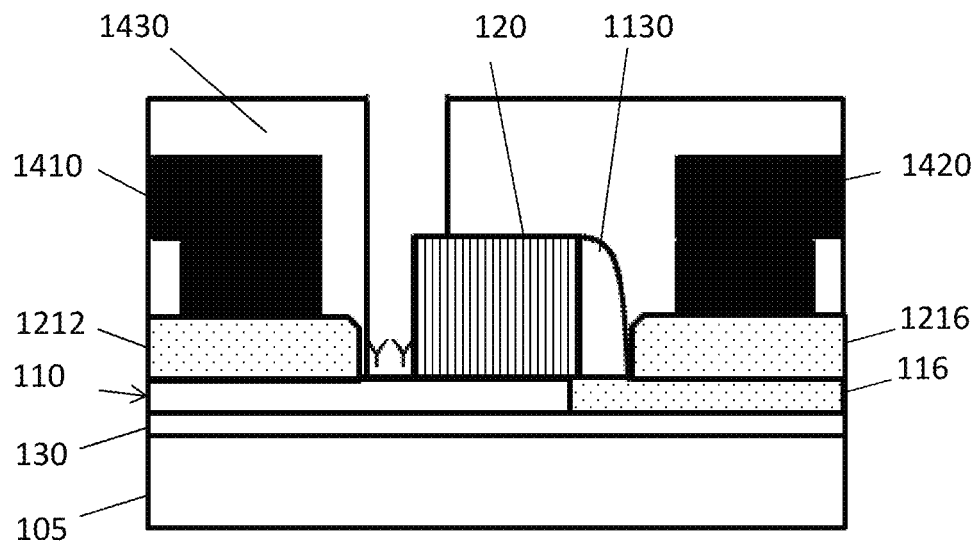
FIG. 19 shows the cross-section AA' of the exemplary embodiment of FIG. 18.

In embodiments of the present disclosure, spacers 1120, 1130 may be provided before providing 250 the doped source region 112 and before providing 240 the doped drain region 116. This way, an underlap region may be created, both between the gate stack 120 and the source region 112, and between the gate stack 120 and the drain region 116. After providing the doped source region 112 and the doped drain region 116, for instance by means of one or more dopant implantation processes, the spacer 1120 next to the gate stack 120 at the side oriented towards the source and/or the spacer 1130 next to the gate stack 120 oriented towards the drain region 116 might be removed. Removing the spacer between the gate stack 120 and the source region 112 results in an underlap region 115 between the gate stack 120 and the source region 112. The width of the underlap region 115 is equal to the width of the spacer 1120 next to the gate stack at the side oriented towards the source 112. In embodiments of the present disclosure the width of the underlap region 115 is larger than 1 nm, for instance between about 1 nm and about 50 nm, or between about 3 nm and about 10 nm. An exemplary embodiment of the present disclosure which is produced by providing 264 at least one spacer next to the gate stack 120, and removing it at the side of the source region, is illustrated in FIG. 19, and will be discussed in more detail below.

Figure 12:
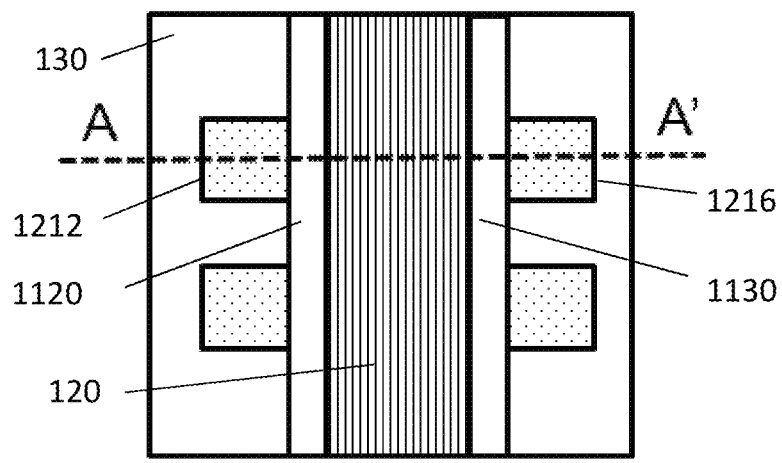
FIG. 12 shows a top view of a semiconductor chip which has a source pad and a drain pad on top of the fins in accordance with embodiments of the present disclosure.
Figure 13:
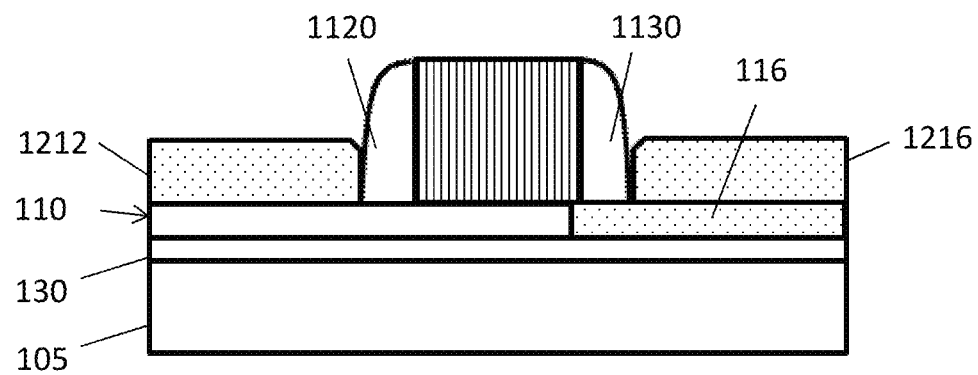
FIG. 13 shows the cross-section AA' of the exemplary embodiment of FIG. 12.

In a method 200 according to embodiments of the present disclosure, providing 250 the doped source region 112 and or providing 240 the doped drain region 116 may comprise a process 266 wherein, rather than performing an implantation process or besides an implantation process, an in-situ doped semiconductor layer is grown. In embodiments of the present disclosure, this way, a doped drain region or part thereof and/or a doped source region or part thereof are provided on or in the substrate, for instance on or in the fin 110, next to the spacer. An exemplary embodiment of the present disclosure is illustrated in FIG. 12 and FIG. 13. These figures show a semiconductor chip as in FIG. 11, but which has a source pad 1212 and a drain pad 1216 on top of the fins 110. The source pad 1212 is located on top of the fins 110 and next to the spacer 1120 at the source side. The drain pad 1216 is located on top of the fins 110 and next to the spacer 1130. As can be seen, in the embodiment illustrated in FIG. 13, the drain is formed by a combination of drain region 116 and drain pad 1216. The source is formed solely by the source pad. In alternative embodiments, also the source could be formed by a combination of a previously implanted doped region and a deposited doped region, and/or the drain could be formed solely by a deposited doped region.

In embodiments of the present disclosure, providing 250 the doped source region and/or providing the doped drain region may comprise, instead of dopant implantation or growing of doped semiconductor layers, applying spin-on-glass, and outdiffusing 268 dopants into the source and/or drain regions.

Figure 14:
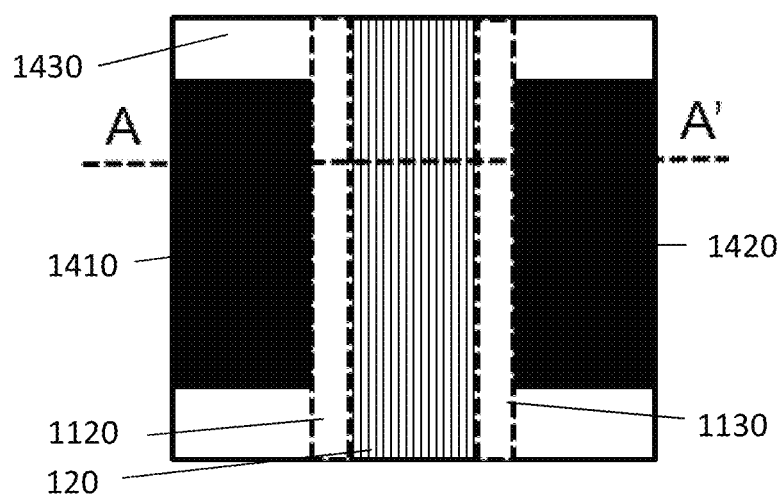
FIG. 14 shows a semiconductor chip configured for biosensing according to an exemplary embodiment of the present disclosure after applying BEOL processing.
Figure 15:
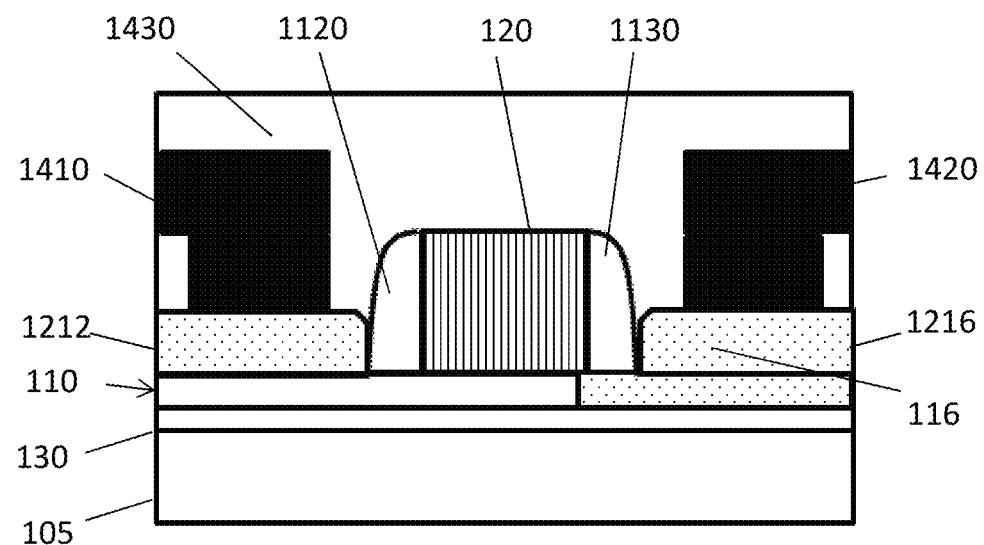
FIG. 15 shows the cross-section AA' of the exemplary embodiment of FIG. 14.

In embodiments of the present disclosure, after having provided the doped source and drain regions, back end of line (BEOL) processing 280 is applied to the semiconductor chip. An example thereof is illustrated in FIG. 14 and FIG. 15 wherein a conductive contact 1410, for instance a metal contact such as e.g. an aluminum contact, is deposited on top of the source, for instance on top of the source pad 1212, and wherein a conductive contact 1420, for instance a metal contact such as e.g. an aluminum contact, is deposited on top of the drain, for instance on top of the drain pad 1216. After depositing the conductive contacts 1410, 1420, an insulating layer 1430 is deposited on top of the semiconductor chip 100.

Figure 16:
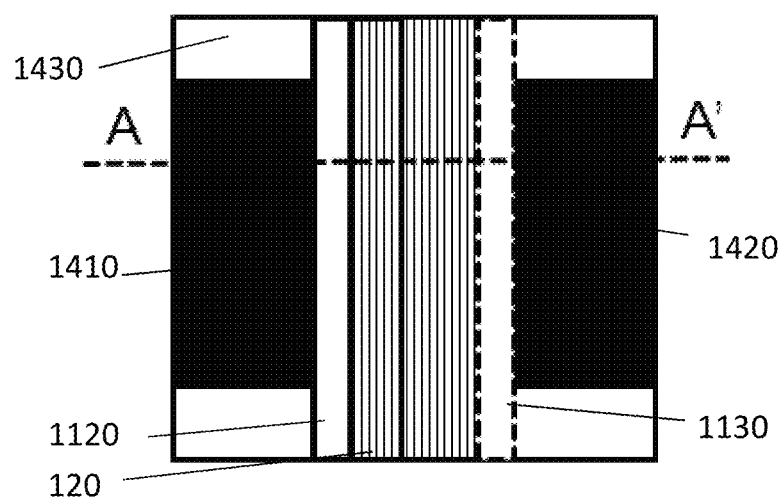
FIG. 16 shows a semiconductor chip configured for biosensing according to an exemplary embodiment of the present disclosure after an intermediate process for opening the insulating layer above the channel in accordance with an embodiment of the present disclosure.
Figure 17:
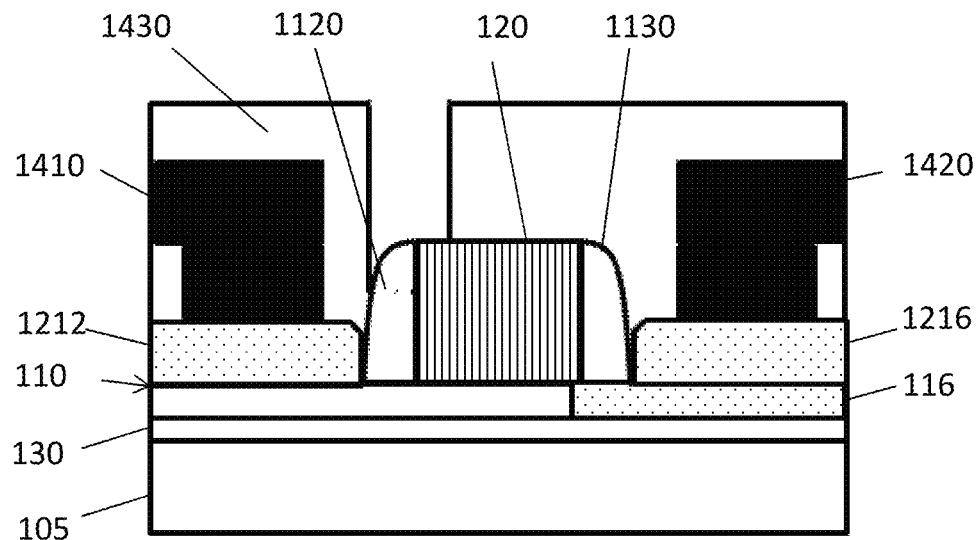
FIG. 17 shows the cross-section AA' of the exemplary embodiment of FIG. 16.

In embodiments of the present disclosure, the insulating layer 1430 is opened above the channel, i.e. that part of the semiconductor layer of the substrate provided between the source and the drain, for instance a portion of the fin 110, at the source side of the semiconductor chip 100, for example above the spacer 1120 located next to the gate stack 120 at the source side of the semiconductor chip 100. An example thereof is illustrated in FIG. 16 and FIG. 17. The opening in the insulating layer 1430 permits contact with the spacer 1120 (or in case no spacer would be present, directly with the channel 114).

Figure 18:
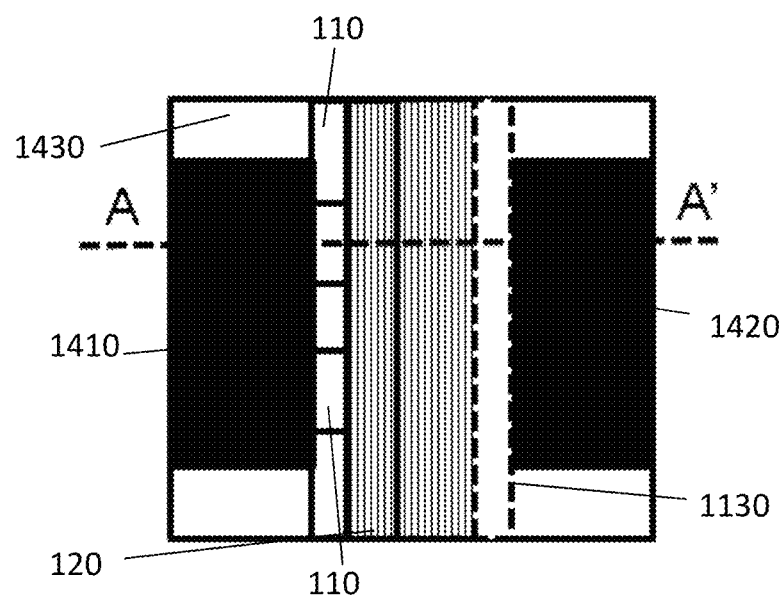
FIG. 18 shows a semiconductor chip in accordance with embodiments of the present disclosure.

In case the opening in the insulating layer 1430 provides access to a spacer 1120, 1130, this spacer 1120, 1130 may be removed 270. This way, a portion of the channel 114 is revealed and uncovered. This uncovered portion provides the underlap 115 between source and gate stack and/or between drain and gate stack. This allows biomolecules to be in direct contact with the channel 114 portion between the gate stack 120 and the source and/or between the gate stack 120 and the drain, when the sensing device is in use. An example thereof is illustrated in FIG. 18 and FIG. 19. By removing 270 the spacer, for instance the spacer 1120 at the source side, the substrate, e.g. the fins 110, become visible in the gap, e.g. at the bottom of the gap, in the insulating layer 1430. In embodiments of the present invention the spacer 1120 may be removed by using any suitable product, for instance an etchant for removing the spacer, such as e.g. phosphoric acid. In the example of FIG. 18 and FIG. 19 the fins 110 at the source side are not doped. As illustrated in FIG. 19 the biomolecules have direct access to the channel 114.

The direct access of biomolecules to the channel 114 is only illustrated in the drawings in FIG. 19 for the embodiment where the underlap is provided by means of a spacer 1120; however, the present disclosure is not limited thereto. Also in the embodiment of FIG. 8, an underlap region 115 is created, this time by means of tilted implantation of dopant elements, and at this underlap region 115 there is a direct access of biomolecules to the channel 114.

In a second aspect, the present disclosure relates to a semiconductor chip 100 for bio-sensing. The semiconductor chip 100 comprises at least one FET device. This may for example be a FinFET device or a TFET device. The FET device comprises a source, a drain, a gate stack 120 and a channel region 114 between the source and the drain. The gate stack 120 is only partially overlapping the channel region 114 at the source side and/or at the drain side, such that there is an underlap region 115 between the source and the gate stack and/or between the drain and the gate stack.

In some embodiments, the underlap region 115 has a semiconductor surface which may be adapted for capturing particular biomolecules, e.g., by having formed thereon molecules having one or more functional groups configured to bind to the particular biomolecules. When the biomolecules are attached to the semiconductor, e.g., through the functional groups, the threshold voltage of the resulting FET device may shift. Moreover, the amount of the shift in the threshold voltage may be proportional to the surface concentration of the biomolecules, thereby allowing for a quantitative sensing of the biomolecules.

Figure 3:
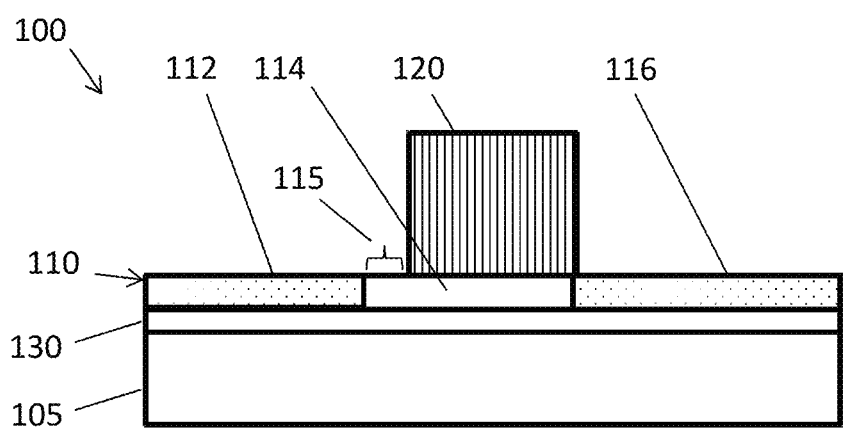
FIG. 3 shows the cross-section AA' of the exemplary embodiment of FIG. 1.

In the particular case of a FinFET device, the FET device comprises a semiconductor fin 110 and a gate stack 120 whereby the gate stack 120 partially overlaps the semiconductor fin 110. In embodiments of the present disclosure a channel 114 is implemented in the fin 110, and a drain 116, 1216 and a source 112, 1212 are implemented in and/or on the fin 110. The gate stack 120 is only partially overlapping the channel 114 at the source side and/or at the drain side. The non-overlapped channel region 115 at the source side and/or drain side is suitable for sensing biomolecules. FIG. 2 is a schematic illustration of the top view of a an exemplary embodiment of the present disclosure. FIG. 3 shows the cross-section AA' of the same exemplary embodiment. The figures show a semiconductor chip 100 for biosensing. The semiconductor chip comprises a FinFET. The FinFET comprises two silicon fins 110 and a gate stack 120 partially overlapping the semiconductor fin 110. In this exemplary embodiment, each fin 110 comprises a source 112, a channel 114, and a drain 116. The gate stack 120 is only partially overlapping the channel 114, such that part of the channel 114 at the source side is not overlapped by the gate stack. The region 115 of the channel which is not overlapped by the gate stack is suitable for sensing biomolecules. In this exemplary embodiment the fins 110 may be made of silicon and they may be located on an oxide layer 130, the oxide layer being on top of a silicon substrate 105.

In embodiments of the present disclosure, a spacer 1130 may be present between the gate stack 120 and the drain 1216 on the fin 110. An example thereof is illustrated in FIG. 19. FIG. 19 also illustrates an embodiment of the present disclosure whereby the gate stack 120 is overlapping the drain 116. In alternative embodiments of the present disclosure, not illustrated in the drawings, a spacer may be present between the gate stack and the source, and the uncovered part of the channel may be present at the drain side.

Embodiments of the present disclosure may comprise a reference FET device, for instance a reference FinFET. The channel of the reference FET device, for example the reference FinFET, may be completely overlapped by the gate stack. The reference FET device, e.g. the reference FinFET, has no opening through which the biomolecules have direct access to the channel 114. The reference FET device, e.g. the reference FinFET, allows to increase the sensitivity of the semiconductor chip even more by comparing the FET measurements, e.g. FinFET measurements, with the reference FET measurements, e.g. reference FinFET measurements.

In embodiments of the present disclosure, the FET device may comprise a backgate.

In embodiments of the present disclosure, the fin 110 of a FinFET device may have an increased body factor. This can for example be obtained by using triangular shaped fins instead of rectangular shaped fins.

In a third aspect the present disclosure relates to the use of a semiconductor chip 100 for biomolecule sensing.

Semiconductor chips according to the present disclosure, have a gate stack 120 which is not completely overlapping the channel 114. The free part 115 of the channel may for instance be located at the source side and is suitable for sensing biomolecules. The free part of the channel is preferably located at the source side because there it has the highest impact. The impact of the underlap at the source side, and thus the impact of the source resistance Rs, is the largest for short gate lengths; for longer channel devices the channel resistance is dominant. Changing the amount of biomolecules at the uncovered part (underlap region) of the channel has the same effect as changing the gate source overlap. Changing the amount of biomolecules at the uncovered part of the channel changes the parasitic series resistance at the source side and therefore changes the drain current.

In embodiments of the present disclosure, the semiconductor chip 100 may be controlled by applying a voltage at the backgate of the semiconductor chip 100 for biasing the semiconductor chip in the sub-threshold region. By adjusting the backgate voltage, the sub-threshold sweep can be modified to increase the sensitivity of the bio-sensing measurements. Lowering the sub-threshold swing by frontgate/backgate coupling can only be done if the channel 114 is undoped. The subthreshold swing is defined as 1/subthreshold slope; so the lower the subthreshold swing, the steeper the characteristic and as such a small variation in voltage can change the current over a large range.

In embodiments of the present disclosure, the steepness of the sub-threshold swing is decreased by using the parasitic bipolar transistor in the FET device, for instance a FinFET device. For that purpose the FET devices, for instance FinFET devices, may be made on a UTBOX substrate. By doing so, the back substrate can be used as a second gate (back gate). By decreasing the thickness of the BOX the capacitance of this backgate is higher and as such lower bias conditions can be used e.g. 1-2V instead of 20-30V in the case of a thick BOX. In embodiments of the present disclosure, the body factor of the fin 110 is increased.

Scaled semiconductor devices have the disadvantage that they are sensitive to random telegraphy noise (RTN). This leads to noisy current measurements and to problems in distinguishing the current variations induced by the biomolecules. The RTN can be reduced by reducing the number of defects as these are capturing and releasing the charges. Therefore the RTN can be reduced by removing implants (e.g. an undoped channel, gentle doping of the source and drain areas). The RTN can also be reduced by reducing the number of defects in the gate dielectric (interface states). This can be done by using $SiO_2$ dielectrics. In embodiments of the present disclosure the RTN is minimized by minimizing the number of impurity atoms in the source and the drain by using solid state doping to make the source 112 and/or drain 116. This can be done by applying a doped SOG (spin-on-glass) layer and afterwards applying outdiffusion of the doped SOG layer into the fin at the source and/or drain regions. The SOG might for example be doped with dopant elements such as B, P, or As. It is an advantage of embodiments of the present disclosure that the RTN can be lowered, for instance by a factor 5 to 10, by minimizing the number of impurity atoms. By lowering the variations in the current caused by RTN, the semiconductor chip 100 becomes more sensitive for variations in the current caused by changing the number of biomolecules at the open side of the channel 114.

Figure 20:
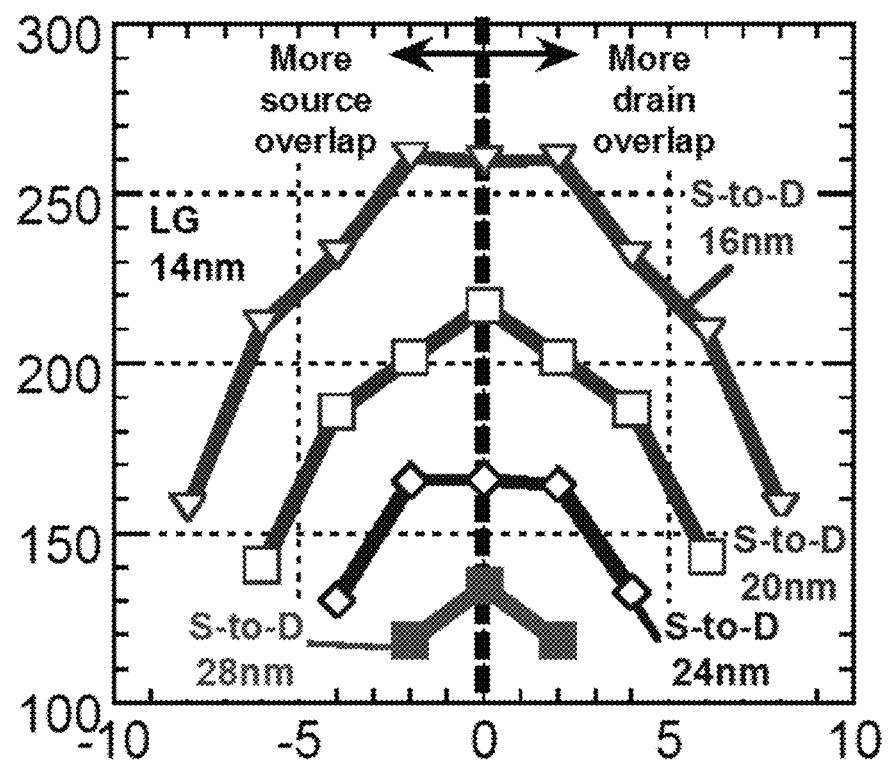
FIG. 20 shows the simulation of the on current Ion in the linear region of a FinFET in accordance with an embodiment of the present disclosure and this in function of the overlap/underlap distance.
Figure 21:
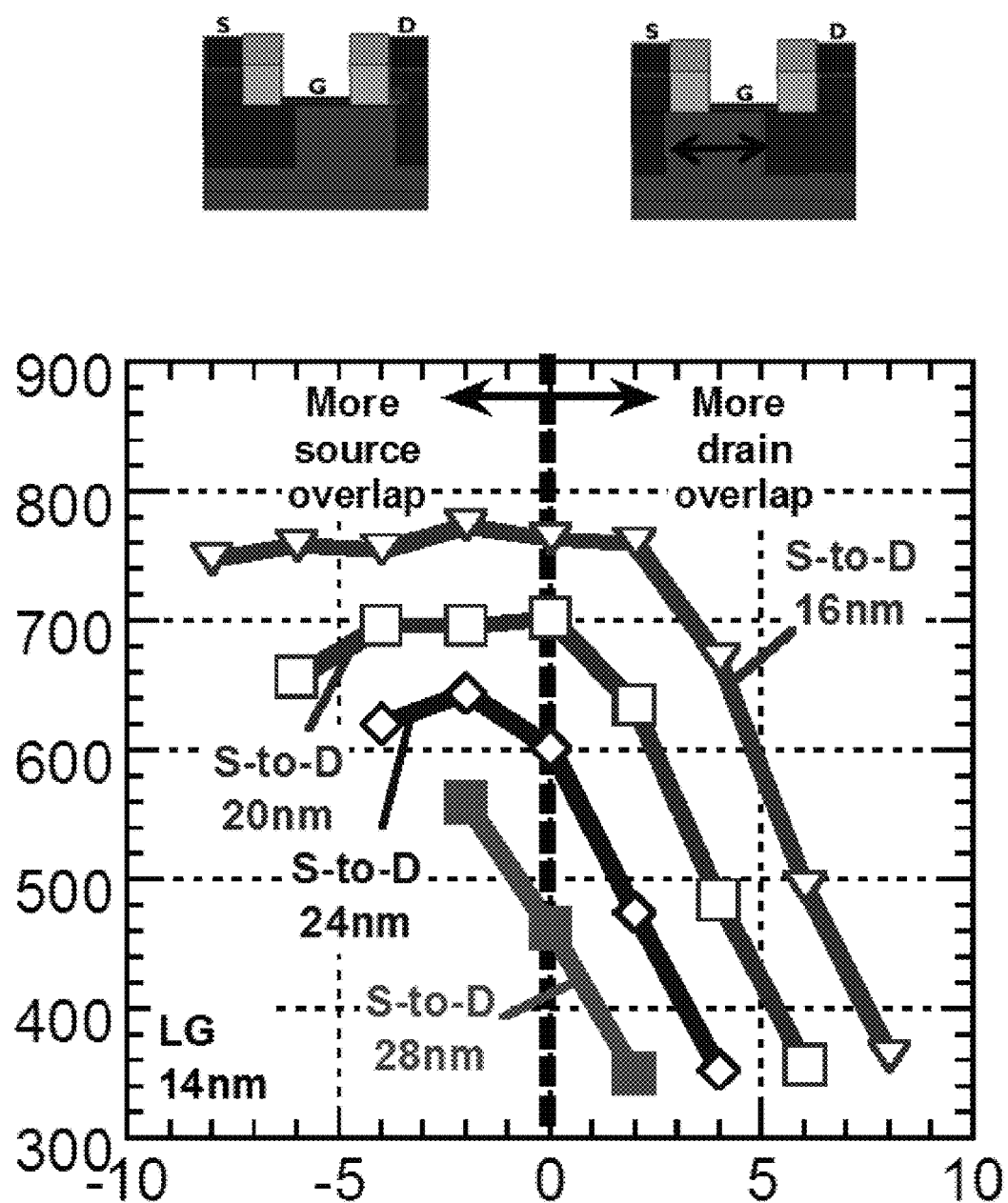
FIG. 21 shows the simulation of the on current Ion in the saturation region of a FinFET in accordance with an embodiment of the present disclosure and this in function of the overlap/underlap distance.

FIG. 20 and FIG. 21 show the on current of a FinFET according to an embodiment of the present disclosure, in function of the overlap of the gate stack 120 over the drain 116 or the source 112. Negative values correspond with a gate stack 120 overlapping the source 112 and underlapping the drain 116 (the overlap/underlap is expressed nm). Positive values correspond with a gate stack 120 overlapping the drain 116 and underlapping the source 112. Overlapping and underlapping is also illustrated in the schematic drawings at the top of FIG. 21. In the left drawing the gate stack 120 is overlapping the source 112 and in the right drawing the gate stack 120 is overlapping the drain 116. FIG. 20 shows the on current in the linear region of the FinFET. FIG. 21 shows the on current in the saturated region of the FinFET. In both figures, from top to bottom curve the following source-drain distances apply: 16 nm, 20 nm, 24 nm, 28 nm. The simulations in these figures are performed for germanium, but the simulations are also applicable for silicon. It can be seen from these simulations that the saturation current is more sensitive to source underlap (the positive values in FIG. 21). Therefore, in accordance with embodiments of the present disclosure, the uncovered part of the channel is preferably located at the source side.

While certain embodiments of the inventions have been described, these embodiments have been presented by way of example only, and are not intended to limit the scope of the disclosure. Indeed, the novel apparatus, methods, and systems described herein may be embodied in a variety of other forms; furthermore, various omissions, substitutions and changes in the form of the methods and systems described herein may be made without departing from the spirit of the disclosure. Any suitable combination of the elements and acts of the various embodiments described above can be combined to provide further embodiments. The accompanying claims and their equivalents are intended to cover such forms or modifications as would fall within the scope and spirit of the disclosure.

What is claimed is:

1. A method of fabricating a semiconductor chip configured for bio-sensing, the method comprising:
   obtaining a substrate comprising at least one semiconductor layer;
   providing a gate stack on the substrate;
   providing a doped drain region in and/or on the substrate; and
   providing a doped source region in and/or on the substrate,
   wherein the doped drain region and/or the doped source region have an underlap region laterally between the gate stack and the source region and/or between the gate stack and the drain region, such that the underlap region is configured for sensing biomolecules attached thereto.

2. The method according to claim 1, wherein providing the doped source region and/or providing the doped drain region includes performing a tilted ion implantation.

3. The method according to claim 1, further comprising, prior to providing the doped source region and/or providing the doped drain region, providing a spacer adjacent the gate stack at a side oriented towards the source region and/or a spacer adjacent the gate stack at a side oriented towards the drain region.

4. The method according to claim 3, wherein providing the doped source region and/or providing the doped drain region comprises growing an in-situ doped semiconductor layer.

5. The method according to claim 3, wherein providing the doped source region and/or providing the doped drain region comprises depositing a doped spin-on glass and outdiffusing dopants from the doped spin-on glass into the source region and/or the drain region.

6. The method according to claim 3, further comprising, after providing the doped source region and/or providing the doped drain region, removing the spacer at the side of the gate stack oriented towards the source region and/or removing the spacer at the side of the gate stack oriented towards the drain region.

7. The method according to claim 1, further comprising back end-of-the-line (BEOL) processing of the semiconductor chip.

8. The method according to claim 1, wherein providing the doped drain region includes covering a source side of the substrate such that the source side is not doped or further doped with a source dopant.

9. A semiconductor chip configured for bio-sensing, the semiconductor chip comprising:
   at least one field-effect transistor (FET) device comprising a source, a drain, a gate stack and a channel region formed between the source and the drain,
   wherein the gate stack partially overlaps the channel region at a source side and/or at a drain side, such that a non-overlapped channel region is formed at the source side and/or at the drain side that is configured for sensing biomolecules.

10. The semiconductor chip according to claim 9, further comprising a spacer formed on the substrate between the gate stack and the drain.

11. The semiconductor chip according to claim 9, wherein the gate stack overlaps the drain.

12. The semiconductor chip according to claim 9, further comprising a reference FET having a gate stack which completely overlaps the channel.

13. The semiconductor chip according to claim 9, wherein the at least one FET comprises a backgate.

14. The semiconductor chip according to claim 9, wherein the channel region has an increased body factor.

15. The semiconductor chip according to claim 9, wherein the non-overlapped channel region comprises a semiconductor surface having formed thereon molecules having functional groups configured to bind to the biomolecules.

16. The semiconductor chip according to claim 9, wherein the channel region is undoped.

17. A method of using the semiconductor chip according to claim 9 for biomolecule sensing.

18. The method of claim 17, wherein the semiconductor chip comprises a backgate, and wherein a sub-threshold sweep is adjusted by adjusting a voltage on the backgate.

* * * * *